United States Patent [19]

Mason et al.

[11] Patent Number: 4,764,463
[45] Date of Patent: Aug. 16, 1988

[54] PLATELET CYROPRESERVATION

[75] Inventors: James M. Mason; David D. Pifer, both of Memphis, Tenn.

[73] Assignee: The University of Tennessee Research Corporation, Knoxville, Tenn.

[21] Appl. No.: 924,964

[22] Filed: Oct. 30, 1986

[51] Int. Cl.⁴ .................. A61K 35/14; A01N 1/02
[52] U.S. Cl. ................................ 424/101; 435/2
[58] Field of Search ..................... 435/2; 424/101

[56] References Cited

U.S. PATENT DOCUMENTS

| 3,296,091 | 1/1967 | Beal, III et al. | |
|---|---|---|---|
| 3,629,071 | 12/1971 | Sekhar. | |
| 3,729,947 | 5/1973 | Higuchi. | |
| 3,996,103 | 12/1976 | Sekhar. | |
| 4,033,816 | 7/1977 | Sekhar. | |
| 4,059,967 | 11/1977 | Rowe. | |
| 4,110,161 | 8/1978 | Sekhar. | |
| 4,251,995 | 2/1981 | Pert. | |
| 4,303,671 | 12/1981 | Fitzpatrick. | |
| 4,365,629 | 12/1982 | Pert et al. | |
| 4,390,619 | 6/1983 | Harmening-Pittiglio. | |
| 4,476,221 | 10/1984 | Kane et al. | 435/2 |
| 4,558,142 | 12/1985 | Holland | 549/465 |

OTHER PUBLICATIONS

Vila et al., Chem. Abst. vol. 104 (1986), p. 146154r.
Johnson et al., Brit. J. Haemotology, vol. 58, No. 1, (1984), pp. 178-179.
G. H. R. Rao et al., Influence of pH on the Prostacyclin ($PGI_2$) Mediated Inhibition of Platelet Function, Prostaglandins and Medicine 4:263-273, 1980.

Primary Examiner—Sam Rosen
Attorney, Agent, or Firm—Luedeka, Hodges & Neely

[57] ABSTRACT

A method for preserving blood platelets by freezing the platelets in contact with a cryoprotectant solution containing a sufficient quantity of prostacyclin for the substantially complete inhibition of platelet function and having a pH which promotes the preservation of the platelets.

14 Claims, 4 Drawing Sheets

PLATELET CYROPRESERVATION

The present invention relates to the preservation of blood platelets for subsequent clinical use and more particularly relates to a method for platelet cryopreservation.

Blood platelets, which are necessary for the clotting of blood, are desired for transfusions to patients with both congenital and drug-induced clotting deficiencies caused by low platelet counts. While platelets are easily separated from whole blood, loss of the hemostatic function over time generally limits the room temperature storage (22° C. optimum temperature) of platelets to a matter of days. Platelet suspensions suitable for transfusion are often in short supply.

To achieve long term storage of blood platelets, various cryopreservation methods have been developed. One such method employs dimethyl sulfoxide (DMSO) as a cryoprotectant in a slow freezing process. However, the toxicity of DMSO requires that the DMSO be removed from thawed platelets prior to use. To eliminate the need for additional preparation of the thawed platelets, platelets have been frozen in acidic glycerol-glucose solutions. While these methods enable the direct transfusion of the thawed platelets, the quantity and quality of the recovered platelets is not sufficiently high for platelet cryopreservation to be widely used.

It is accordingly an object of the present invention to provide a method for platelet cryopreservation which improves the quantity and quality of the recovered platelets. It is a further object of the method to produce a platelet preparation upon thawing which can be safely used for platelet transfusions without additional preparation. It is yet another object to provide a method for platelet cryopreservation which is suitable for routine use by blood bank technicians.

These and other objects and advantages of the invention are described in the following written description and accompanying drawings in which:

FIG. 1 is a graph of morphology results obtained with the method of the present invention as performed in the Example compared with fresh platelets, platelets stored at room temperature and platelets preserved by another platelet cryopreservation method (results identified by "*" relate to platelets preserved in accordance with the method of U.S. Pat. No. 4,251,995).

Figure 1:
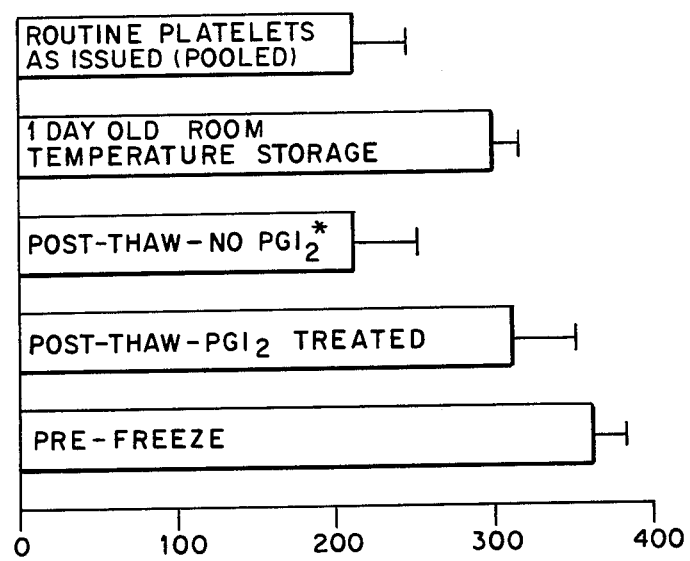

It has surprisingly been found the platelets can be preserved for extended periods by freezing the platelets in contact with a cryoprotectant solution containing sufficient prostacyclin to substantially completely inhibit platelet function and having a pH which promotes the preservation of the platelets. In accordance with a preferred form of the invention, a platelet concentrate to be cryopreserved is prepared from platelet rich plasma in the presence of sufficient prostacyclin to substantially completely inhibit platelet function. The frozen platelet preparation produced in accordance with the invention may be stored for extended periods and, upon thawing, contains a high yield of functioning platelets and which can be safely transfused to humans.

Prostacyclin ($PGI_2$) is a member of a class of compounds referred to as prostaglandins which are associated with the regulation of smooth muscle activity, lipid metabolism, and reproductive physiology. Prostacyclin is a potent stimulator of adenylate cyclase, which results in increased cyclic AMP and inhibition of platelet function. Under acidic conditions and in weakly basic solutions such as normal blood plasma, prostacyclin spontaneously decomposes with a half-life of about 15 minutes at pH 7.4.

During freezing in accordance with the invention, it is necessary to maintain the level of the prostacyclin in the cryoprotectant solution at a level sufficient for the substantially complete inhibition of platelet function. Because of decomposition of prostacyclin in the cryoprotectant solution, the quantity of prostacyclin must be sufficient initially so that a sufficient quantity remains throughout the freezing process. Preferably, a minimum necessary amount is employed which produces inhibition since an excess may interfere with the aggregation after transfusion. A suitable amount has been found to be approximately 30 ug per platelets in a blood unit in a cryoprotectant at pH 7.4. It will be understood that the amount is variable depending on the composition and pH of the cryoprotectant solution. Although unnecessary, it is believed to be possible to use prostacyclin stabilizers such as albumin in the cryoprotectant solution so long as they do not affect the activity of the platelets upon transfusion or otherwise affect the preservation of the platelets.

The pH of the cryoprotectant solution during freezing must be maintained at a level which facilitates the preservation of the platelets. Thus, the pH must be limited to below about 8.0 even though prostacyclin is unstable at low pH levels. However, the rapid decomposition of prostacyclin at low pH makes it impractical to use a pH of less than about 7.0. Because the optimum environment for preservation is achieved when the pH approximates the physiological pH of blood plasma, it is preferable to employ a cryoprotectant solution having a pH of between about 7.2 and about 7.6.

The cryoprotectant solution employed in the invention is an aqueous solution with an osmolarity value consistent with platelet preservation and containing constituents for promoting the preservation of the platelets during the freezing process while also being compatible with prostacyclin. In addition, it is desirable for the cryoprotectant solution to permit the direct transfusion of thawed platelets with no preparation other than resuspension in plasma. The preferred cryoprotectant solution is a glycerol-glucose saline solution such as the solution disclosed in U.S. Pat. No. 4,059,967, the disclosure of which is incorporated herein by reference. It is desirable to use such a cryoprotectant solution with a pH in accordance with the present invention having between about 4 and about 7 weight percent glycerol and between about 2 and about 6 weight percent glucose.

In order to achieve the desired pH of the cryoprotectant solution, it is generally necessary to employ a compound which functions as a pH buffer which is otherwise compatible with the platelets and prostacyclin and which preferably is suitable for direct transfusion of the platelets to human subjects. In the preferred glycerol-glucose cryoprotectant solution, a suitable buffer is sodium citrate. It is desirable to maintain the concentration of sodium citrate at a level which does not adversely affect the osmolarity of the cryoprotectant.

Freezing of the platelets is preferably achieved by containing the platelets in the cryoprotectant solution in plastic bags and forming the bags into a generally planar configuration so that the heat transferred during freezing is generally consistent throughout the cryoprotectant solution. It is particularly desirable to employ the controlled freezing method disclosed in U.S. Pat. No. 4,251,995, the disclosure of which is incorporated herein by reference. The freezing bags are placed in a cassette with two corrugated cardboard sheets adjacent the freezing bag and two metal plates in contact with the cardboard. The cassette is frozen by immersing in liquid nitrogen with the resulting freezing rate being about −20° C. to about −30° C. per minute.

Before freezing of the platelets in contact with the cryoprotectant solution according to the present invention, it is preferable to prepare a platelet concentrate in which the platelets from one unit of blood are suspended in about 5 to 15 ml of liquid. A suitable platelet concentrate can be prepared from platelet rich plasma which is separated by centrifugation from a unit of blood which has been collected into an anti-coagulant solution such as CPDA-1 (Citrate-Phosphate-Dextrose-Adenine). The concentrate is prepared from the platelet rich plasma by further centrifugation under conditions which prevent platelet aggregation.

In the preferred form of the invention, aggregation of the platelets during preparation of the concentrate is prevented by the presence of sufficient prostacyclin in the platelet rich plasma to substantially inhibit platelet function. Since the prostacyclin inhibits platelet function at the normal pH of the plasma, there is no need to adjust the pH to approximately 6.5 as is commonly done before centrifugation to produce the concentrate. The concentrate is suitable for freezing in the cryoprotectant without any large adjustment of the pH before freezing which could create an undesirable increase in osmolarity in the cryoprotectant solution. It has been found that a suitable amount of prostacyclin in the platelet rich plasma to achieve this result is 70 ug per platelets in one unit of blood which can be achieved by direct addition of prostacyclin to the platelet rich plasma.

Formation of the platelet concentrate in accordance with the preferred form of the invention is advantageously carried out by resuspending the platelets from one unit of blood in a small quantity of the supernatant plasma, e.g., 5 to 15 ml. The cryoprotectant solution is formed by adding to the concentrate, the prostacyclin and a concentrated solution having the constituents of the cryoprotectant solution, which when mixed with the plasma in the concentrate, produces the desired cryoprotectant solution. For example, a concentrate containing approximately 8% glucose, 10% glycerol, and 0.04M sodium citrate can be mixed with equal volumes of the platelet concentrate to produce the cryoprotectant solution. The prostacyclin to be present in the cryoprotectant solution is preferably added to the platelet concentrate before the cryoprotectant solution is formed but also can be present in the concentrated solution provided that it is added immediately before that solution is mixed with the platelet concentrate. Thus, in the preferred form of the invention, the platelets are maintained in the presence of at least some prostacyclin prior to and during freezing.

To prepare the frozen platelets for use, the platelets are merely thawed, preferably quickly. This is suitably accomplished, for example, by immersing the same bags in which they were frozen in a water bath at room temperature (20° to 25° C.). Plasma or a synthetic plasma substitute can be added to the platelets to resuspend them for transfusion and this suspension is suitable for direct transfusion. The prostacyclin is labile in the plasma and the inhibition of platelet function due to the prostacyclin will essentially disappear upon transfusion.

The invention can be more readily understood and appreciated when reference is made to the following example which illustrates an embodiment of the invention without any intent to limit the invention to the embodiment disclosed.

EXAMPLE

Preparation of Platelet Concentrate

Platelets were prepared from eighteen fresh units of whole blood collected in plastic bags containing CPDA-1 anticoagulant and the platelets from each unit were frozen in accordance with the following procedures within 6 hours of collection. The units were centrifuged in a Sorvall RC-3 centrifuge for 10 minutes at 1800 RPM and 22° C. The platelet-rich plasma (PRP) was removed to a satellite bag and approximately 70 ug of prostacyclin (UpJohn, Kalamazoo, MI) were added. The PRP was then centrifuged for 10 minutes at 4100 RPM and 22° C. Most of the supernatant platelet-poor plasma (PPP) was removed, leaving a concentrate volume between 7 and 15 ml. The PPP was frozen for use as a diluent when the platelets were thawed.

Freezing Procedure

An additional 30 ug of prostacyclin were added and the platelets were manually resuspended to produce a platelet concentrate. A concentrated cryoprotectant solution was prepared by dissolving 80 g of glucose, 100 ml of glycerol, and 11.75 g sodium citrate.$2H_2O$ in a total volume of 1 liter using sterile water. The platelet concentrate was transferred to a polyolefin freezing bag sold under the trademark PHARMAFLEX by Pharmachem, Bethlehem, PA. The outer plastic bag in which the freezing bag was shipped was reserved and used to hold the freezing cassette assembly during the freezing process. An equal volume of the concentrated cryoprotectant solution was added resulting in a final volume of 15–30 ml to be frozen. All air was expressed and the bag was sealed.

Each platelet concentrate bag was placed between hinged sheets of corrugated cardboard (single-wall, bursting strength 19.4 kg/$cm^2$, C flute obtained from Longview Fibre Co., Amsterdam, NY.) with the ports away from the hinge. Each sheet measured 13.3 by 15.2 cm. Between the cardboard sheets, the concentrate bags assumed a V-shaped configuration, the geometry of which assures that the concentrate will freeze from the bottom up, with no pockets of liquid trapped within the bag. The cardboard sheets also served to control the rate of heat transfer to between about −20° C. and about −30° C./minute during freezing and to protect the unit during storage. The cardboard-freezing bag assembly was put between hinged 0.64 cm thick aluminum plates, which served to maintain the V-shaped configuration of the concentrate bag and to moderate heat transfer during freezing. The entire assembly was placed in the plastic shipping bag reserved earlier and allowed to equilibrate at room temperature for 15 minutes. The top of the outer bag was folded twice and the folded edge was pierced by two cup hooks attached to a ½-inch wooden dowel. The outer plastic bag prevents the platelet concentrate bag from coming into direct contact with the liquid nitrogen and prevents the formation of gaseous nitrogen on the aluminum plates, which would alter the rate of freezing by acting as an insulator. The suspension device allowed the freezing cassette to be submerged in the liquid nitrogen while preventing entry of liquid nitrogen into the bag. After 15 minutes in the liquid nitrogen, the outer plastic bag and metal cassette were removed and the concentrate bag and its cardboard protector were transferred to an aluminum holder for storage at −150° C. in the vapor phase of a liquid nitrogen freezer.

Thawing and Reconstitution

The freezing bag was removed from its cardboard cover and thawed in 22° C. water with minimal agitation. Immediately after thawing, some units were divided into two equal aliquots for reconstitution. One aliquot was prepared using autologous or ABO-compatible PPP reserved during the preparation process as the diluent. A second aliquot was prepared using a synthetic post-thaw diluent (PD) of 0.5 ml dextrose in 57 ml of the solution sold under the trademark PLASMALYTE by Travenol, Deerfield. IL. Other units were reconstituted using PPP only. Reconstitution was accomplished by adding diluent to the concentrates in three stages with gentle rocking during addition of diluent and incubations at room temperature between additions. In the first step, a volume of diluent equal to the volume of concentrate was added over a three-minute period and the platelets were allowed to equilibrate for 15 minutes at room temperature. In the second step the volume of diluent added was doubled. The dilution was again done over a three-minute period and was followed by a 10 minute equilibration period. The third step was identical to the second. After all diluent was added, the concentrations were allowed to equilibrate for an additional 30 minutes before samples were taken for evaluation of platelet structure and function. Additional samples were collected on five concentrates after thawing and after each addition of diluent, to determine platelet activation during reconstitution.

Platelet Yield and Morphology

Post-thaw yield was calculated by comparing the pre-freeze and post-thaw platelet counts. Pre-freeze counts were performed instrumentally using a Baker 210 platelet analyzer (Baker Diagnostics, Bethlehem, PA). Because of reported spurious instrumental counts on thawed platelets, post-thaw counts were performed manually by phase microscopy. Post-thaw yield of the platelets from the 18 units is shown in Table 1 expressed as percent recovery.

TABLE 1

| Unit | % Yield |
|---|---|
| 1 | 97 |
| 2 | 79 |
| 3 | 88 |
| 4 | 98 |
| 5 | 90 |
| 6 | 111 |
| 7 | 95 |
| 8 | 61 |
| 9 | 107 |
| 10 | 132 |
| 11 | 94 |
| 12 | 101 |
| 13 | 93 |
| 14 | 94 |

TABLE 1-continued

| Unit | % Yield |
|---|---|
| 15 | 105 |
| 16 | 112 |
| 17 | 134 |
| 18 | 87 |
| Avg. | 98.8 |

Changes in platelet morphology were assessed by examining the platelets according to the morphology scoring method of Kuniki et al., Transfusion, Vol, 15, pp. 414–421 (October 1975). Each platelet was classified by shape and assigned a numerical value: 4 points for those platelets which maintained a normal discoid appearance, 2 for those which had undergone a shape change to a spherical form, 1 for those with observable dendritic projections, and 0 points for platelets which had released the contents of their granules and were seen only as greatly enlarged membrane ghosts. The values for the two hundred platelets were totaled and divided by two to give the morphology score for that preparation. Random pre-freeze concentrates, platelets preserved according to the method disclosed in U.S. Pat. No. 4,251,995, and pools of one-day old and 1–5 day old room temperature-stored banked platelets were also scored as controls. FIG. 1 shows graphically the morphology results observed.

Platelet Aggregation

Figure 2:
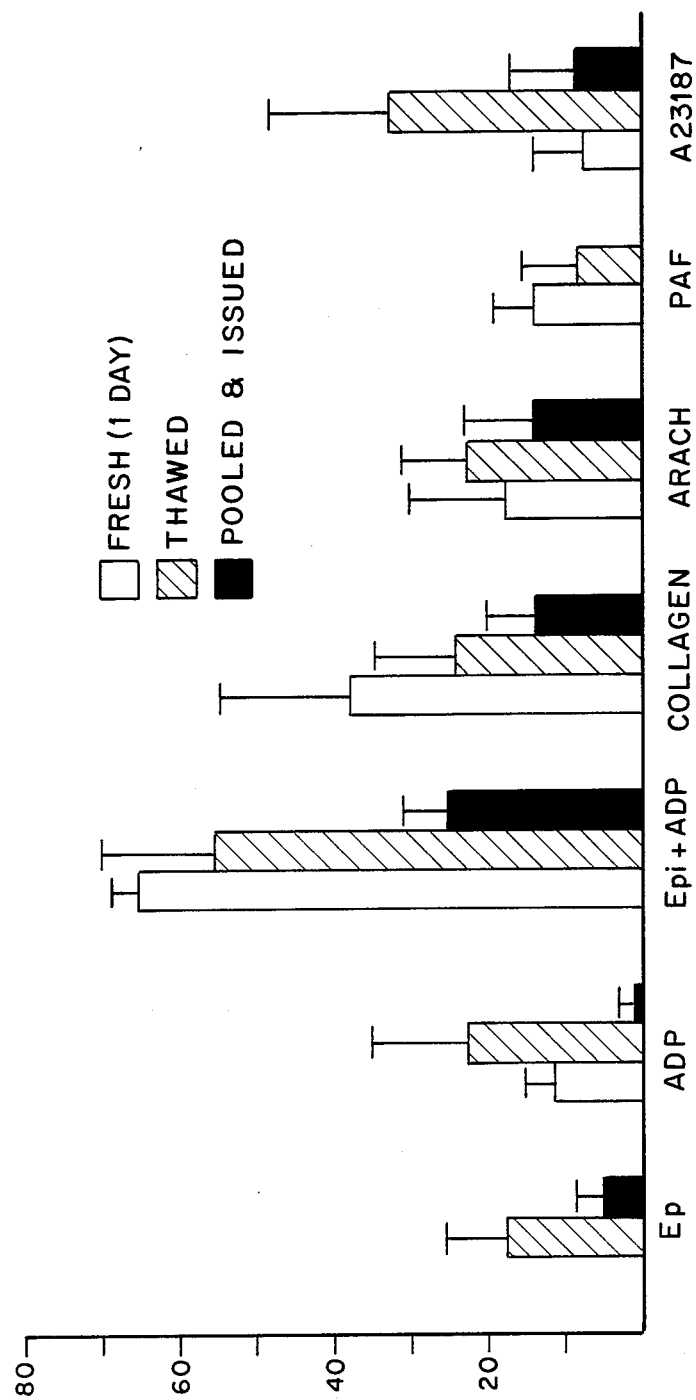
FIG. 2 is a graph showing observed aggregability results of the Example compared with results observed with room temperature stored platelets.

Platelet aggregation was measured on a Payton Dual Channel Aggregometer, Payton Associates, Inc., Buffalo, NY, according to the method of Born, J. Physiol. 168, 178–95 (1963). The count of the platelet concentrates was adjusted to $250$–$350 \times 10^6$/ul with PPP for aggregation and all other in vitro platelet function studies. Various aggregating agents were added to 0.5 ml of PRP at 37 C. with continuous stirring. Light transmission was measured to determine the degree of aggregation. As aggregates formed, more light was transmitted through the PRP. Aggregating agents, used at final concentrations selected to give maximum aggregation, were: 10 uM ADP (Sigma), 55 uM epinephrine (Sigma), 8 ug/ml fibrillar equine tendon collagen reagent (Horman-Chemie Co., Munich, FRG), 2 ug/ml A23187 (Cal Biochem Behring, San Diego, CA), 500 ug/ml arachidonic acid (NuCheck Preparations, Inc., Elysian, MN), and 800 nM platelet aggregating factor (PAF, Bachem Feinchemikalien, Bubesdorf, Switzerland). Human fibrinogen, grade L, 95% clottable (Kabi, Stockholm, Sweden) was added to the concentrates reconstituted in PD. In addition to assessing the effect of each agent singly, a synergistic aggregation mechanism was studied by adding first epinephrine, then ADP to the PRP. Aggregation studies were performed at 0, 3, and 5 hours post-thaw for some concentrates to assess the possible effects of $PGI_2$ remaining in the thawed and reconstituted product. The aggregability results with one-day old and 1–5 day old routinely issued platelets as controls are shown graphically in FIG. 2.

Serotonin Uptake and Release

Figure 3:
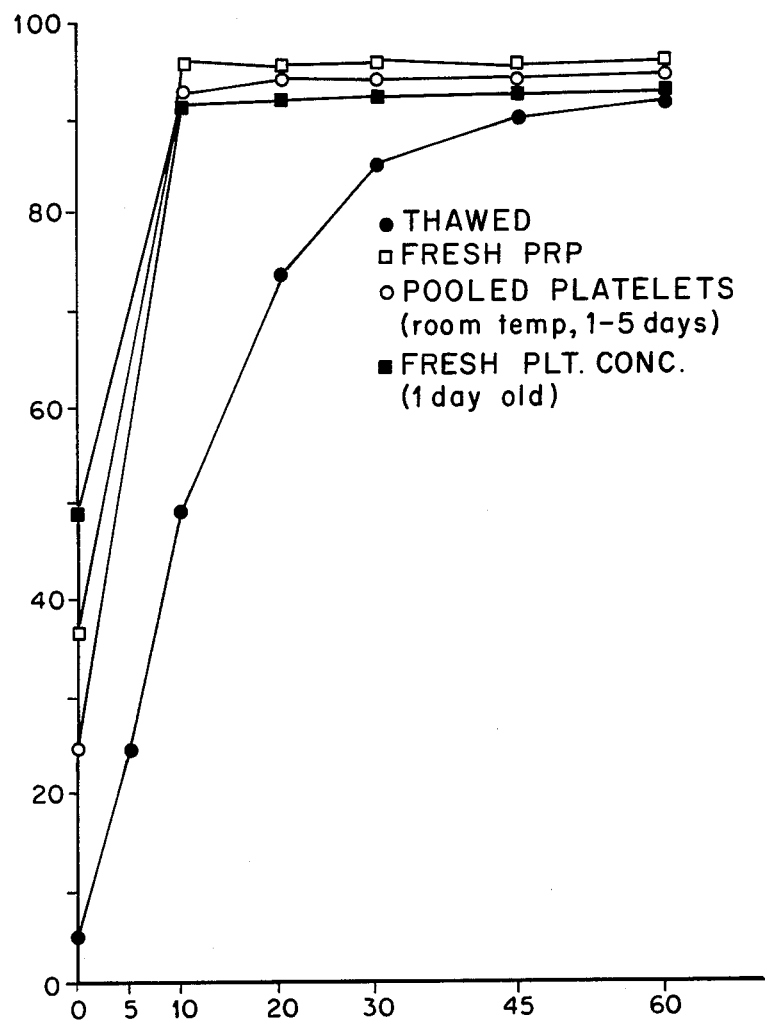
FIG. 3 is a graph showing observed serotonin uptake results of the Example compared with results obtained with fresh platelet rich plasma and room temperature stored platelets.

Serotonin uptake and release were studied as an evaluation of the function of the platelets' dense granules. PRP ($250$–$350 \times 10^6$ platelets/ml) was mixed by inversion with 1 ul/ml PRP $^{14}C$-Serotonin [5-hydroxy(side chain-2-$^{14}C$)tryptamine creatinine sulfate aqueous solution+2% ethanol], 57.4 mCi/mmol activity (Amersham, Arlington Heights, IL). The amount of radioactivity expressed as counts per minute (CPM) in 0.1 ml of the PRP was counted on a Beckman model LS-1800 liquid scintillation counter (Beckman Instruments, Inc., Irvine, CA) to determine the total amount of labeled serotonin present. After 37° C. incubations of 0, 5, 10, 20, 30, 45, and 60 minutes, 0.5 ml aliquots were removed and centrifuged, and 0.1 ml of supernatant was removed. Radioactivity in the supernatant was measured as above. CPM in the supernatant was subtracted from total CPM to determine the amount of labeled serotonin associated with the platelets. This figure was divided by total CPM so that uptake could be expressed as a percentage. Observed percent serotonin uptake is shown in FIG. 3 with fresh PRP and routine pooled platelets as controls.

Figure 4:
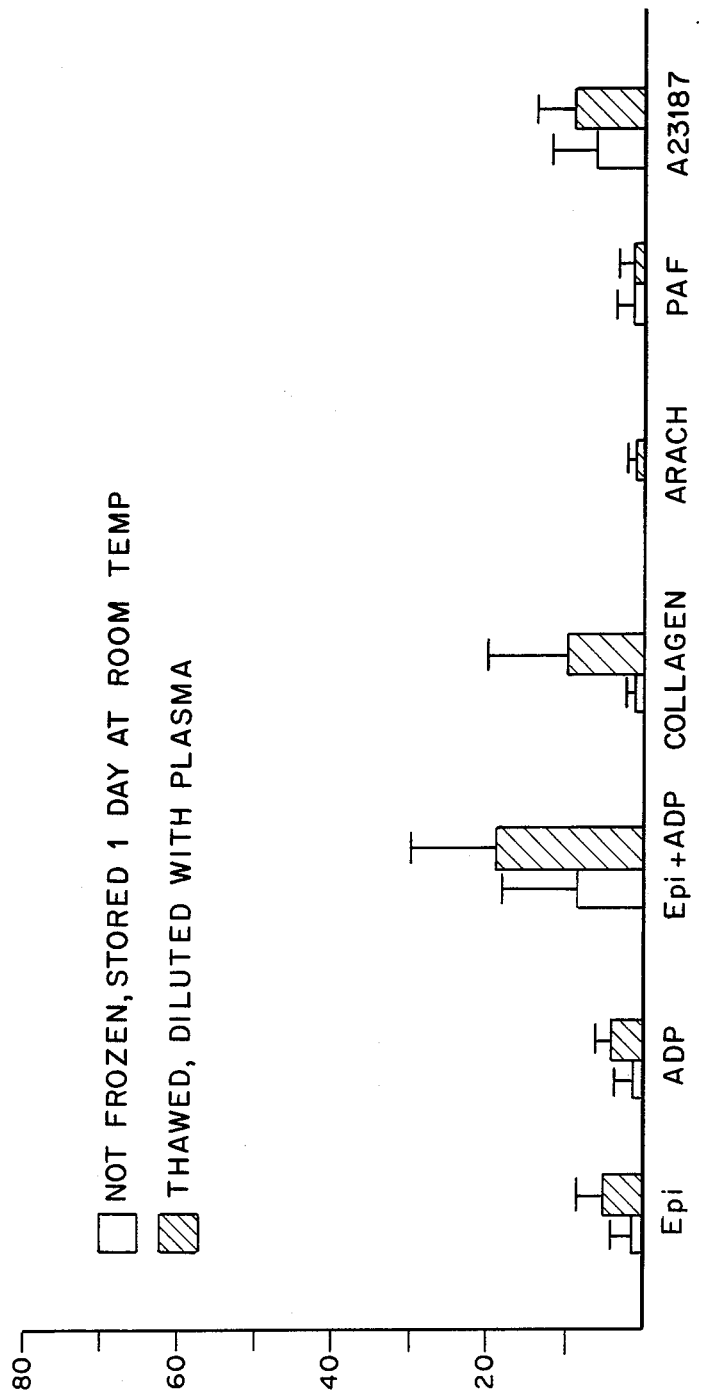
FIG. 4 is a graph showing observed serotonin release results of the Example compared with the results obtained with room temperature stored platelets.

To measure serotonin release, PRP was first incubated with $^{14}$C-Serotonin for 45 minutes to allow serotonin uptake to come to equilibrium. 0.5 ml aliquots of this PRP were then stirred at 37 C. for 10 minutes with the same agents used for aggregation studies to stimulate the dense granules to release their serotonin. The concentrates were centrifuged, and the amount of radioactivity in 0.1 ml of supernatant was measured on the liquid scintillation counter. CPM in the supernatant was divided by the CPM associated with the platelets to determine the percentage of serotonin released. Observed percent serotonin release is shown in FIG. 4 with one-day old platelets as controls.

The platelet cryopreservation method according to the present invention improves the yield, morphology, hemostatic function, and serotonin uptake and release of thawed platelets when compared with known cryopreservation methods. In addition, the method of the invention provides platelets with better morphology and aggregability scores compared with one-day old pooled platelets stored at room temperature. Serotonin uptake and release are not affected. Since prostacyclin has been safely infused to humans and the morphology and aggregability of the thawed platelets is better than with platelets stored at room temperature, platelets preserved in accordance with the present invention are well-suited for transfusion to human recipients.

We claim:

1. A method for platelet cryopreservation comprising freezing platelets in contact with an aqueous saline cryoprotectant solution containing between about 4% and about 7% by weight glycerol and between about 2% and about 6% by weight glucose and containing sufficient prostacyclin to substantially completely inhibit platelet function throughout the freezing process, said cryoprotectant solution having a pH of between about 7.2 and about 7.6.

2. The method of claim 1 wherein prostacyclin is present in the cryoprotectant solution at a minimum level necessary to achieve substantially complete inhibition of platelet function throughout the freezing process.

3. The method of claim 1 wherein said freezing is performed at a rate of at least about −20° C. per minute.

4. A method of producing and cryopreserving a platelet concentrate comprising:
producing a platelet concentrate by concentrating platelet rich plasma in the presence of sufficient prostacyclin to substantially completely inhibit platelet function; and
freezing said platelet concentrate in contact with a cryoprotectant solution containing sufficient prostacyclin to substantially completely inhibit platelet function throughout the freezing process, said cryoprotectant solution having a pH of between about 7.0 and about 8.0.

5. The method of claim 4 wherein the pH of the cryoprotectant solution is between about 7.2 and about 7.6.

6. The method of claim 4 wherein said cryoprotectant solution is an aqueous saline solution containing between about 4% and about 7% by weight glycerol and between about 2% and about 6% by weight glucose.

7. The method of claim 4 wherein prostacyclin is present in the cryoprotectant solution at a minimum level necessary to achieve substantially complete inhibition of platelet function throughout the freezing process.

8. The method of claim 4 wherein said freezing is performed at a rate of at least about −20° C. per minute.

9. The method of claim 4 wherein said concentrating of the platelet rich plasma in the presence sufficient prostacyclin to produce a platelet concentrate is performed by adding said prostacyclin to the platelet rich plasma and centrifuging to separate platelets from a supernatant plasma followed by removing at least some of the supernatant plasma.

10. The method of claim 4 wherein said step of concentrating the platelet rich plasma in the presence of prostacyclin to produce said platelet concentrate comprises adding said prostacyclin to the platelet rich plasma, centrifuging to separate platelets from a supernatant plasma, removing at least some of the supernatant plasma, and resuspending in a portion of said supernatant plasma to produce said platelet concentrate.

11. The method of claim 10 further comprising the following steps prior to the freezing of the platelets in contact with a cryoprotectant solution:
adding the prostacyclin to be present during freezing to the platelet concentrate;
adding a concentrate solution containing the constituents of the cryoprotectant solution and a pH buffer to the prostacyclin-containing platelet concentrate to produce the cryoprotectant solution.

12. The method of claim 11 wherein said concentrated solution contains sufficient glycerol and glucose to produce a cryoprotectant solution containing between about 4% and about 7% by weight glycerol and between about 2% and about 6% glucose.

13. The method of claim 11 wherein said concentrated solution contains sufficient sodium citrate to result in a cryoprotectant solution having a pH of between about 7.2 and about 7.6.

14. A frozen platelet preparation for use upon thawing prepared by freezing platelets in the presence of an aqueous saline cryoprotectant solution containing between about 4% and about 7% by weight glycerol and between about 2% and about 6% by weight glucose and containing sufficient prostacyclin to substantially inhibit platelet function throughout the freezing process and having a pH of between about 7.2 and about 7.6.

* * * * *